(12) United States Patent
Inoue et al.

(10) Patent No.: US 6,770,475 B1
(45) Date of Patent: Aug. 3, 2004

(54) PROMOTERS

(75) Inventors: Yasushi Inoue, Tsukuba (JP); Naoya Fushimi, Tsukuba (JP); Hiroyuki Mizubuchi, Tsukuba (JP); Yoshie Yamamoto, Tsukuba (JP); Yoshie Ohshima, Tsukuba (JP); Nozomu Yasutake, Tsukuba (JP); Shinsuke Miyoshi, Tsukuba (JP)

(73) Assignee: Showa Sangyo Co., Ltd., Tokyo (JP)

( * ) Notice: Subject to any disclaimer, the term of this patent is extended or adjusted under 35 U.S.C. 154(b) by 0 days.

(21) Appl. No.: 09/936,145

(22) PCT Filed: Mar. 8, 2000

(86) PCT No.: PCT/JP00/01415

§ 371 (c)(1),
(2), (4) Date: Sep. 7, 2001

(87) PCT Pub. No.: WO00/53778

PCT Pub. Date: Sep. 14, 2000

(30) Foreign Application Priority Data

Mar. 8, 1999 (JP) .............................. 11-060904
Oct. 6, 1999 (JP) .............................. 11-286034

(51) Int. Cl.⁷ .......................... C12N 15/00; C12N 1/20; C12Q 1/00; C07H 21/02; C07H 21/04
(52) U.S. Cl. ..................... 435/320.1; 435/6; 435/69.1; 435/252.3; 435/325; 435/252.5; 536/23.1; 536/24.1
(58) Field of Search ................. 435/4, 6, 69.1, 435/252.3, 252.5, 320.1, 325, 69.2, 183, 200, 201–204; 536/23.1, 24.1, 242

(56) References Cited

FOREIGN PATENT DOCUMENTS

JP 10-262683 A 10/1998
JP 10-327887 A 12/1998

OTHER PUBLICATIONS

Palva et al. (Gene, 1981, vol. 15:43–51).*
Messing, J., *Methods in Enzymology*, 101: 20–78 (1983), Academic Press, Inc.
Mandel, M., et al., "Calcium–dependent Bacteriophage DNA Infection", *J. Mol. Biol.* 53: 159–162 (1970).
Hanahan, D., "Studies on Transformation of Escherichia coli with Plasmids", *J. Mol. Biol.* 166: 557–580 (1983).
Contente, S. et al., "Characterization of Plasmid Transformation in Bacillus subtills: Kinetic Properties and the Effect of DNA Conformation", *Molec. gen. Genet.* 167: 251–258 (1979).
Chang, S. et al., "High Frequency Transformation of Bacillus subtilis Protoplasts by Plasmid DNA", *Molec. gen. Genet.* 168: 111–115 (1979).

* cited by examiner

Primary Examiner—Manjunath N. Rao
(74) Attorney, Agent, or Firm—Webb Ziesenheim Logsdon Orkin & Hanson, P.C.

(57) ABSTRACT

A promoter having a higher activity than that of an α-amylase promoter of a microorganism of the genus Bacillus can be provided by introducing at least one restriction site sequence in the vicinity of the 3' end of the promoter of the α-amylase derived from the microorganism of the genus Bacillus.

10 Claims, 11 Drawing Sheets

PROMOTERS

BACKGROUND OF THE INVENTION

1. Field of the Invention

The present invention relates to promoters. More specifically, the present invention relates to novel promoters having restriction enzyme cleavage site sequences in the vicinity of the 3' end downstream of the promoters and improved promoter activity.

2. Description of the Prior Art

To produce substances with microorganisms, the following operations are widely performed: inserting a gene encoding a desired protein into a vector and introducing the obtained recombinant vector into a cell to express this gene, thereby producing the desired protein in the host microorganism. One of the regions involved in the expression of the gene is a promoter.

The promoter includes a region including −35 and −10 regions which RNA polymerase recognizes and binds to and a region that designates the binding of ribosome to mRNA synthesized by RNA polymerase. Not only the nucleotide sequence of the promoter region is very important regarding expression efficiency, but the length of the nucleotide sequence thereof, that is, the number of bases, is also important (Mol. Gen. Genet. 186 339-(1982)).

Research of the nucleotide sequence of the promoter was first conducted with promoters of E. coli, leading to production of promoters for mass expression of proteins, and substance production using E. coli as a host has been performed.

However, since E. coli produces pyrogens, purification process in protein production is very expensive. Therefore, E. coli is not a suitable host for the fields of pharmaceuticals, foods, or the like, so that other host cells (microorganisms) are in demand. Among these, microorganisms of the genus Bacillus seem promising, because they have been used in fermentation industry, have high secretion performance, and are free from pathogenicity and do not produce pyrogens.

There are a number of reports regarding the production of protein using microorganisms of the genus Bacillus as a host. However, in most cases, the main purpose lies in ligating a gene encoding a desired protein to a secretory signal sequence in-frame for the purpose of secretion (e.g., Japanese Laid-Open Patent Publication (Tokkai) Nos. 59-205996, 62-215393, and 3-206889, Japanese Patent Publication (Tokko) No. 6-69377, and Japanese Laid-Open Patent Publication (Tokkai) No. 7-155183). Thus, there is substantially no attempt to enhance promoter activity.

Regarding improvement of the promoters of the genus Bacillus, Japanese Laid-Open Patent Publication (Tokuhyo) No. 6-500689 describes a hybrid promoter of α-amylase of Bacillus subtilis, and Japanese Laid-Open Patent Publication (Tokuhyo) No. 7-504085 describes that a promoter having nine mutations at the $553^{th}$ and from the $588^{th}$ to $595^{th}$ positions of an α-amylase promoter gene of Bacillus licheniformis has higher activity than the natural sequence. However, the activity of the promoter does not appear to be sufficient.

Thus, there are substantially no reports on research results regarding improvement of promoters of the genus Bacillus. This seems be not because research has not been conducted, but because good results substantially cannot be attained. This seems to be one factor that prevents microorganisms of the genus Bacillus from being utilized as a recombinant host.

Therefore, in particular, in the field of pharmaceuticals or foods, it is desired at present to increase the expression efficiency of promoters of microorganisms of the genus Bacillus, and to increase the utility value of the microorganisms of the genus Bacillus as a host.

Therefore, it is an object of the present invention to provide highly active promoters of microorganisms of the genus Bacillus and to increase utilization of the microorganism of genus Bacillus as a host.

SUMMARY OF THE INVENTION

In order to solve the above problems, the inventors of the present invention found that promoter activity is improved by providing a mutation in a DNA sequence located in the vicinity of the 3' end of an α-amylase promoter region derived from Bacillus amyloliquefaciens and thus attained the present invention.

More specifically, the present invention is directed to a promoter of α-amylase derived from a microorganism of the genus Bacillus, wherein a sequence having at least one restriction enzyme cleavage site (hereinafter, referred to as "restriction site") is introduced between the vicinity of the 3' end of the promoter and an initiation codon of protein, and the activity of the promoter is higher than that of a natural promoter.

In a preferable embodiment, the promoter of α-amylase is derived from Bacillus amyloliquefaciens.

In a preferable embodiment, the restriction site is a restriction site for BamHI.

In a more preferable embodiment, the promoter has the sequence of Sequence ID No. 1.

In another preferable embodiment, the restriction site includes restriction sites for BamHI and at least one restriction site other than the restriction site for BamHI, and the restriction site other than the restriction site for BamHI is present downstream of the BamHI restriction site.

In a more preferable embodiment, the restriction site sequence has a sequence of restriction sites for BamHI and EcoRI, and may have a sequence of at least one restriction site between the BamHI and EcoRI cleavage sites.

In an even more preferable embodiment, the sequence of the promoter is the sequence of Sequence ID No. 2, and the restriction sites are restriction sites for BamHI, SmaI, KpnI, SacI and EcoRI in this order from the 5' end.

In another preferable embodiment, the restriction site sequence has a sequence of restriction sites for BamHI, NdeI, and XhoI in this order from the 5' end.

The present invention is also directed to an expression cassette having the above-described promoter.

Furthermore, the present invention is also directed to an expression vector in which a gene encoding protein is inserted into a restriction site of this expression cassette.

In a preferable embodiment, the sequence encoding protein is a sequence of an intracellular enzyme.

In a more preferable embodiment, the sequence encoding protein is a sequence of phosphorylase or isomerase.

In an even more preferable embodiment, the phosphorylase is trehalose phosphorylase or maltose phosphorylase.

In another preferable embodiment, the isomerase is mannose isomerase.

The present invention is further directed to a recombinant microorganism having the above-described expression vector and a method for producing protein including the step of culturing this recombinant microorganism.

DETAILED DESCRIPTION OF THE INVENTION

Promoter

Figure 1:
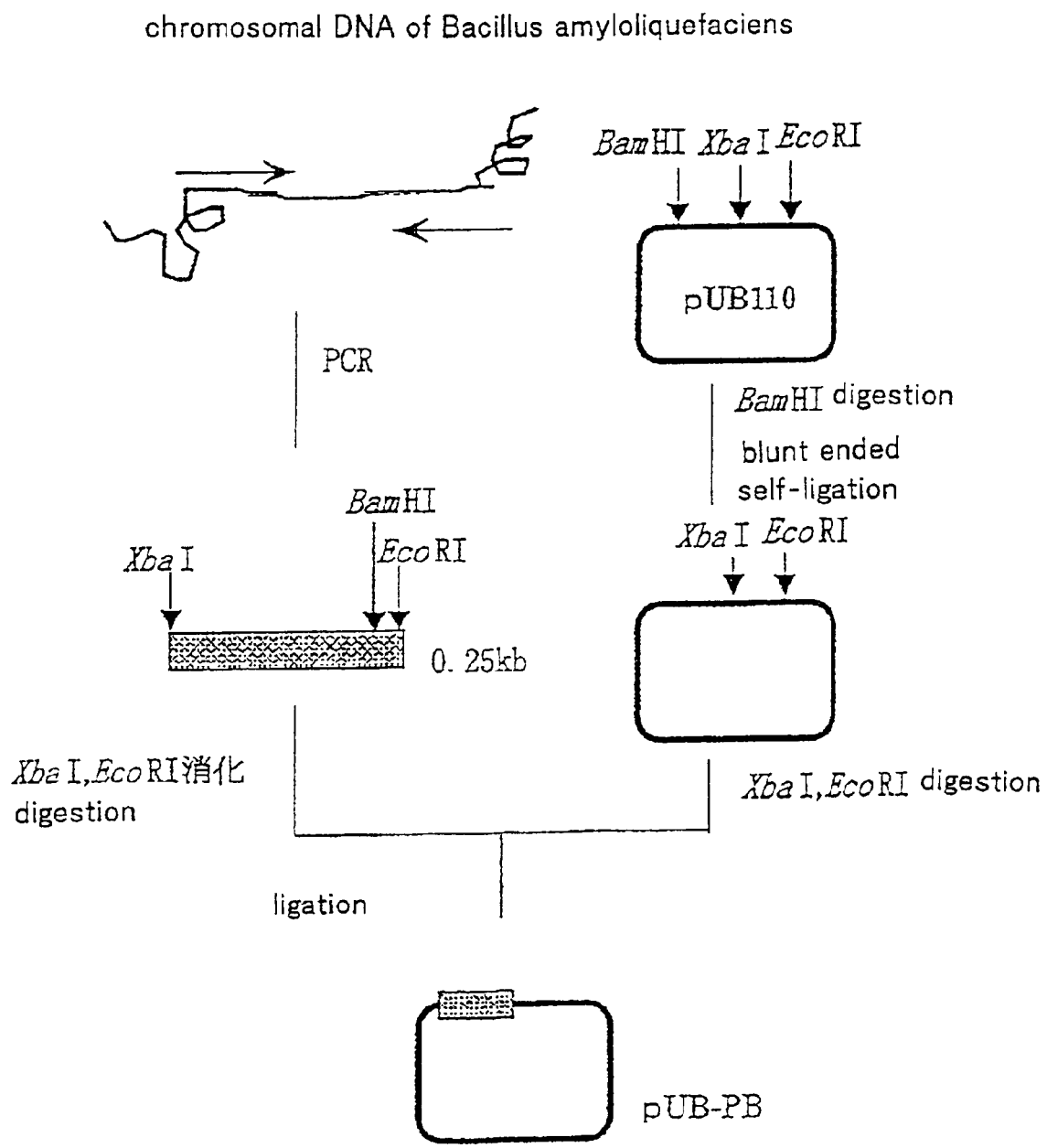
FIG. 1 is a schematic view showing to obtain a promoter and construction of an expression cassette of the present invention.

A promoter of the present invention is obtained by modifying a promoter of α-amylase derived from a microorganism of the genus Bacillus. Examples of microorganisms of the genus Bacillus include *Bacillus amyloliquefaciens, Bacillus subtilis, Bacillus licheniformis, Bacillus polymyxa, Bacillus stearothermophilus, Bacillus thermoproteolyticus, Bacillus coagulans, Bacillus thuringiensis, Bacillus megaterium, Bacillus cereus, Bacillus natto* and *Bacillus acidocaldarius*. Among these, a promoter of α-amylase derived from *Bacillus amyloliquefaciens* is preferable in view of expression efficiency.

In the promoter of α-amylase of the present invention, a sequence having at least one restriction site is introduced between the vicinity of the 3' end and the initiation codon of protein. Herein, "the vicinity of the 3' end" refers to about 10 bp from the 3' end. There is no particular limitation regarding the kind of restriction sites, and examples thereof include restriction sites for BamHI, SmaI, KpnI, SacI, EcoRI, HindIII, PstI, NdeI and XhoI. In the case of one restriction site, the site for BamHI is preferable. In the case of a plurality of restriction sites, it is preferable that the promoter has at least one BamHI site and has other restriction sites downstream thereof. In this case, the site for EcoRI is preferable as another restriction site, and at least one restriction site for, for example, SmaI, KpnI and SacI may be provided between the restriction sites for BamHI and EcoRI. Of course, the promoter may further have another restriction site for, for example, HindIII and PstI downstream of EcoRI.

Moreover, a sequence including restriction sites for BamHI, NdeI and XhoI in this order from the 5' end can be preferably used.

When the promoter of the present invention is used for an expression cassette or an expression vector described below, a plurality of restriction sites may be used as multi-cloning sites. In other words, a plurality of restriction sites can be provided in order to facilitate insertion of foreign genes. The restriction sites of the foreign gene to be inserted can be determined in view of the restriction sites (multi-cloning site) of a vector.

A preferred sequence of the promoter of the present invention is the sequence described in the Sequence ID No.1. This sequence has a BamHI cleavage site sequence in the 3' end. A preferred sequence having two or more restriction sites (i.e., multi-cloning sites) is described in the Sequence ID No.2. In the 3' end of this sequence of Sequence ID No.2, restriction sites for BamHI, SmaI, KpnI, SacI and EcoRI are provided in this order.

The promoter of the present invention can be obtained by introducing a restriction site sequence into the vicinity of the 3' end in the promoter region of α-amylase derived from a microorganism of the genus Bacillus. An appropriate method for gene recombination can be used to introduce a restriction site sequence. For example, a method such as PCR using a primer having a restriction site sequence may be applicable. PCR is preferable because promoter isolation and introduction of a restriction site sequence can be performed at the same time. Primers for PCR can be produced, based on a promoter sequence of α-amylase derived from, for example, *Bacillus amyloliquefaciens* described in Gene 15 43-(1981), and a restriction site sequence can be introduced into the antisense primer sequence (the 3' end primer). The sequences of Sequence ID Nos. 4 and 5 are examples of primers for introducing a restriction site.

Expression Cassette

In the present invention, "expression cassette" refers to a vector or a plasmid that has at least one site for inserting a desired gene to be expressed and in which the desired gene can be expressed when it is inserted. The promoter region of the present invention has a restriction site for inserting a desired gene in its 3' end. Therefore, an expression cassette can be constructed by introducing the promoter of the present invention to an appropriate site of an appropriate vector or plasmid.

Any vector can be used as a vector used to prepare an expression cassette, as long as it can self replicate in a host cell and can retain a promoter sequence and a structural gene encoding a desired protein stably. It is preferable that this vector has a selective marker (e.g., drug resistant genes such as ampicillin resistant gene and kanamycin/neomycin resistant gene) in order to confirm that the vector has been introduced into a host. Moreover, an expression regulation sequence such as an appropriate terminator, enhancer or the like can be ligated thereto. Examples of appropriate terminators include a terminator sequence of α-amylase (Gene 15, 43(1981)).

Examples of vectors of the genus Bacillus used to prepare the expression cassette include pUB110 (Pro. Natl. Acad. Sci. U.S.A., 75, 1423-(1978)), pC194, pT127 (Pro. Natl. Acad. Sci. U.S.A., 74, 1680-(1977)), which can replicate in *Bacillus subtilis*, and derivatives thereof.

Other examples of vectors used to produce the expression cassette include a shuttle vector pHY300PLK (Jpn. J. Genet., 60 235-(1985)), which can replicate in *E. coli* and *Bacillus subtilis*, and further pBR322 (Gene, 2, 95-(1977)) and pUC19 (Messing, Methods. Enzymol., 101, 20-(1983)), which can replicate in *E. coli*.

In particular, shuttle vectors are useful in view of gene amplification.

Expression Vector

In the present invention, an "expression vector" refers to a vector or a plasmid in which a structural gene encoding a desired protein is inserted in the restriction site of the above-described expression cassette. Any gene can be inserted, as long as it can be expressed in a host to which the gene is introduced. Examples thereof include genes of phosphorylase (trehalose phosphorylase, maltose phosphorylase, kojibiose phosphorylase, cellobiose phosphorylase, laminaribiose phosphorylase, etc.). In particular, examples of genes derived from the genus Bacillus include trehalose phosphorylase (hereinafter abbreviated as Tpase) derived from *Bacillus stearothermophilus* SK-1 strain (deposited with the International Patent Organism Depository, National Institute of Bioscience and Human-Technology, Agency of the Industrial Science and Technology, Ministry of International Trade and Industry Japan, 1-1-3, Tsukuba Higashi, Ibaraki, JAPAN (original Deposit date: Sep. 29, 1994), FERM BP-5594) and maltose phosphorylase (hereinafter abbreviated as MPase) derived from Bacillus species RK-1 strain (deposited with the International Patent Organism Depository, National Institute of Bioscience and Human-Technology, Agency of the Industrial Science and Technology, Ministry of the International Trade and Industry Japan, 1-1-3, Tsukuba Higashi, Ibaraki, JAPAN (original Deposit date: Jul. 12, 1995), FERM BP-5592). Examples of genes of microorganisms of other genus than the genus Bacillus include mannose isomerase (hereinafter abbreviated as MIase) derived from Agrobacterium radiobactor M36 (deposited with the International Patent Organism Depository, National Institute of the Bioscience and Human-Technology, Agency of Industrial Science and Technology, Ministry of International Trade and Industry Japan, 1-1-3, Tsukuba Higashi, Ibaraki, JAPAN (original Deposit date: Apr. 23, 1999), FERM P-17377. The Agrobacterium radiobactor M36 FERM P-17377 was transferred to the Depository under Budapest Treaty, the International Patent Organism Depository, National Institute of Bioscience and Human-Technology, Agency of the Industrial Science and Technology, Ministry of the International Trade and Industry Japan, 1-3, Higashi 1-chome, Tsukubashi, Ibaraki-ken, JAPAN, and assigned International Deposit No. FERM BP-7206 on Jul. 5, 2000 (original Deposit date: Apr. 23, 1999).

The foreign genes are ligated not only for the purpose of obtaining gene products encoded by the genes, but also for other purposes in the case where protein is not synthesized (e.g., regulation of expression by anti-sense RNA).

The gene encoding a desired protein may or may not include a so-called leader sequence that is involved in secretion. In the case of the former, the desired protein is secreted outside the host cell, and in the case of the latter, the desired protein is stored in the host cell.

A structural gene encoding a desired protein is inserted into an expression cassette by a suitable method used by those skilled in the art. When the sequence of the restriction enzyme cleavage site of the promoter of the present invention matches the sequence in the 3' end and the 5' end of the gene to be introduced, the gene can be introduced into the restriction enzyme cleavage site. When they do not match, the sequence of the restriction site of the expression cassette can be changed so as to match the sequence of the gene to be introduced, or the sequence at the end of the gene to be introduced can be changed. The sequence can be changed by PCR, site-specific mutation or other methods. The above-described recombinant DNA technology can be performed, for example, with reference to Molecular Cloning A Laboratory Manual (Cold Spring Harbor Laboratory, 1989).

(Method for Producing Recombinant Microorganism and Desired Protein)

Then, the obtained expression vector is introduced into a host microorganism. There is no particular limitation regarding the host microorganism. For example, in the case of *E. coli*, DH5α strains, HB101 strains, C600 strains, JM101 strains and the like can be used. In the case of the genus Bacillus, strains such as *Bacillus subtilis*, BD170, 168, ISW1214 can be used. Microorganisms of the genus Bacillus are most preferable because the promoter is derived from a microorganism of the genus Bacillus.

There is no limitation regarding a method for introducing the expression vector to a host microorganism. Examples thereof include transformation, transduction, cell fusion, and electroporation. For example, in the case of the *E.coli* host, the method of Mandel and Higa (J. Mol. Biol., 53,159-(1970)), the method of Hanahan (J. Mol. Biol., 166, 557-(1983)) or the like can be used. In the case of microorganisms of the genus Bacillus, a competent cell method (Mol. Gen, Genet., 167, 251-(1979)), a protoplast method (Mol. Gen, Genet., 168,111-(1978)) or the like can be used.

After the introduction, a recombinant microorganism is selected with a selective marker, and the obtained recombinant microorganism is cultured, so that the desired protein is secreted in a medium, or stored in the microorganism cells. Then, the desired protein can be recovered by a conventional method.

Comparison between the promoter activity of the present invention and the activity of the natural promoter sequence is performed by measuring the amount of expression of the foreign gene inserted downstream of the promoter.

EXAMPLES

Hereinafter, the present invention will be described more specifically by way of examples, but the present invention is not limited thereto.

Example 1

Obtaining the Promoter of the Present Invention and Construction of an Expression Cassette FIG. 1 shows a schematic view for obtaining the promoter of the present invention and construction of an expression cassette, Bacillus amyloliquefaciens IFO 15535 was cultured and chromosomal DNA was extracted by a conventional method. Two kinds of primers having sequences of Sequence ID Nos. 3 and 4 in the sequence listing were synthesized based on the sequence of the promoter of α-amylase described in Gene, 15, 43-(1981), and used to amplify the DNA by PCR with chromosomal DNA described above. The PCR was performed using AmpliTaqGold (manufactured by Perkin-Elmer Corp.) as thermostable polymerase with GeneAmp PCR System 9700 (manufactured by Perkin-Elmer Corp.), according to the manufacturer's instructions.

A gene fragment that had been amplified by PCR was cleaved with restriction enzymes XbaI and BamHI, and then subjected to 3.0% agarose gel electrophoresis. Thus, a 0.25 kbp XbaI-BamHI fragment including the promoter region of α-amylase was recovered from the agarose gel. By determining the sequence of the obtained fragment, it was found that the sequence of the third and second positions from the 3' end of the promoter sequence of the original α-amylase gene was changed from AA to TC, and thus a BamHI cleavage site was introduced.

Separately, a plasmid pUB110 (manufactured by SIGMA Co.) was digested with XbaI and BamHI, and then the obtained promoter sequence (0.25 kbp XbaI-BamHI fragment) was ligated thereto with T4DNA ligase, so that an expression cassette pUB-PB was obtained (FIG. 1).

Example 2

Obtaining the Promoter of the Present Invention and Construction of an Expression Cassette.

Figure 2:
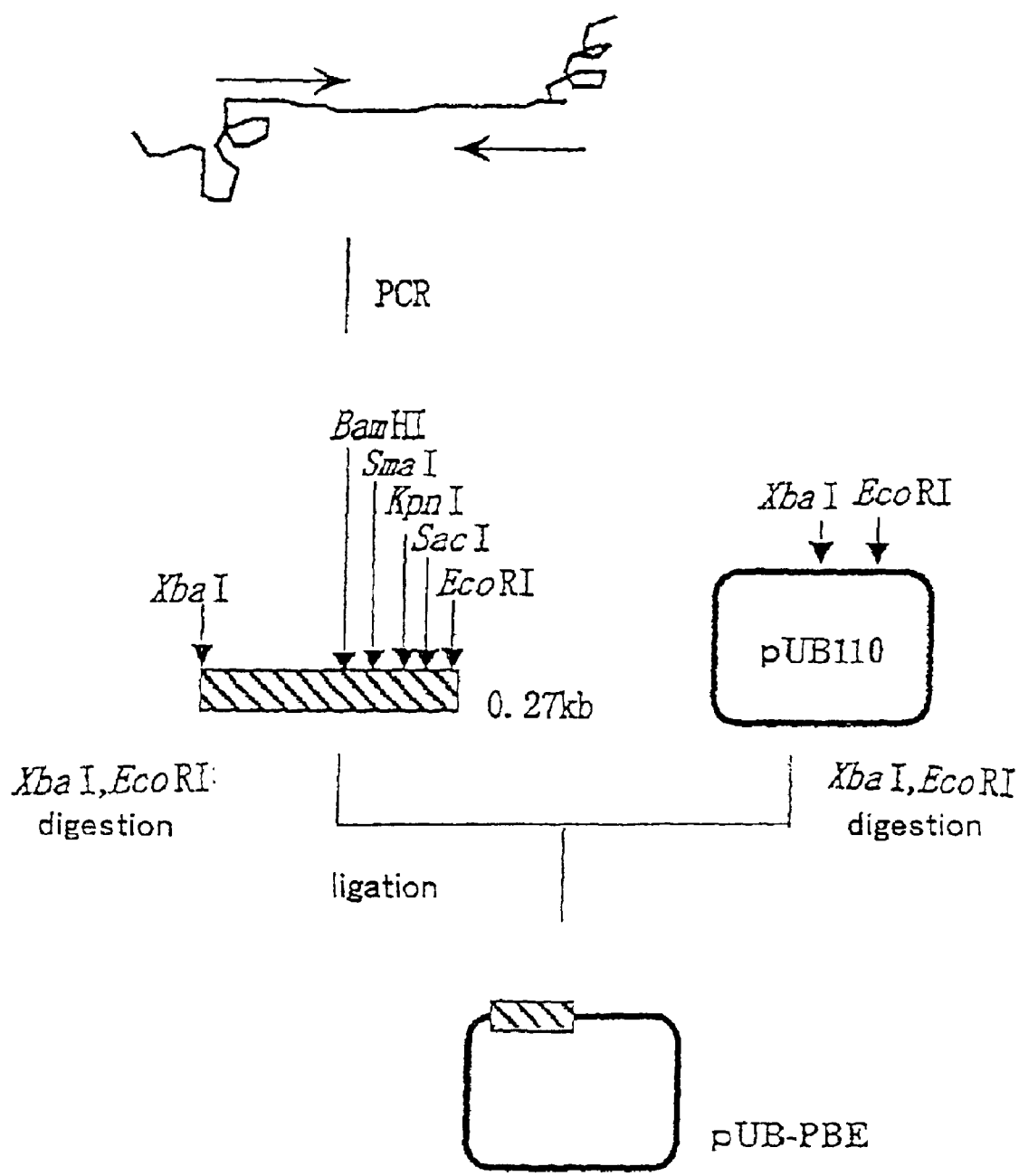
FIG. 2 is a schematic view of construction of an expression cassette pUB-PBE of the present invention.

The same operations were performed except that the primer of the sequence indicated by Sequence ID No. 5 was used instead of Sequence ID No. 4. Then, a DNA fragment (0.27 kbp XbaI-EcoRI DNA fragment) in which restriction sites for SmaI, KpnI, SacI, and EcoRI were introduced downstream of the sequence of Sequence ID No. 1 was introduced into a plasmid pUB110 cleaved with XbaI and EcoRI. Thus, an expression cassette pUB-PBE was obtained. FIG. 2 shows a schematic view of the construction of this expression cassette pUB-PBE.

Example 3

Construction of MPase Expression Vector

An MPase gene was obtained from chromosomal DNA of Bacillus species RK-1 strain (FERM P-15044), based on the description of Japanese Laid-Open Patent Publication (Tokkai) No. 10-262683. More specifically, a gene was amplified by PCR, using two kinds of primers having sequences of Sequence ID Nos. 6 and 7 in the sequence listing, cleaved with restriction enzymes BamHI and EcoRI, and then subjected to 0.8% agarose gel electrophoresis. Thus, a 2.4 kbp BamHI-EcoRI fragment was recovered. This fragment contained the structural gene of MPase.

Figure 3:
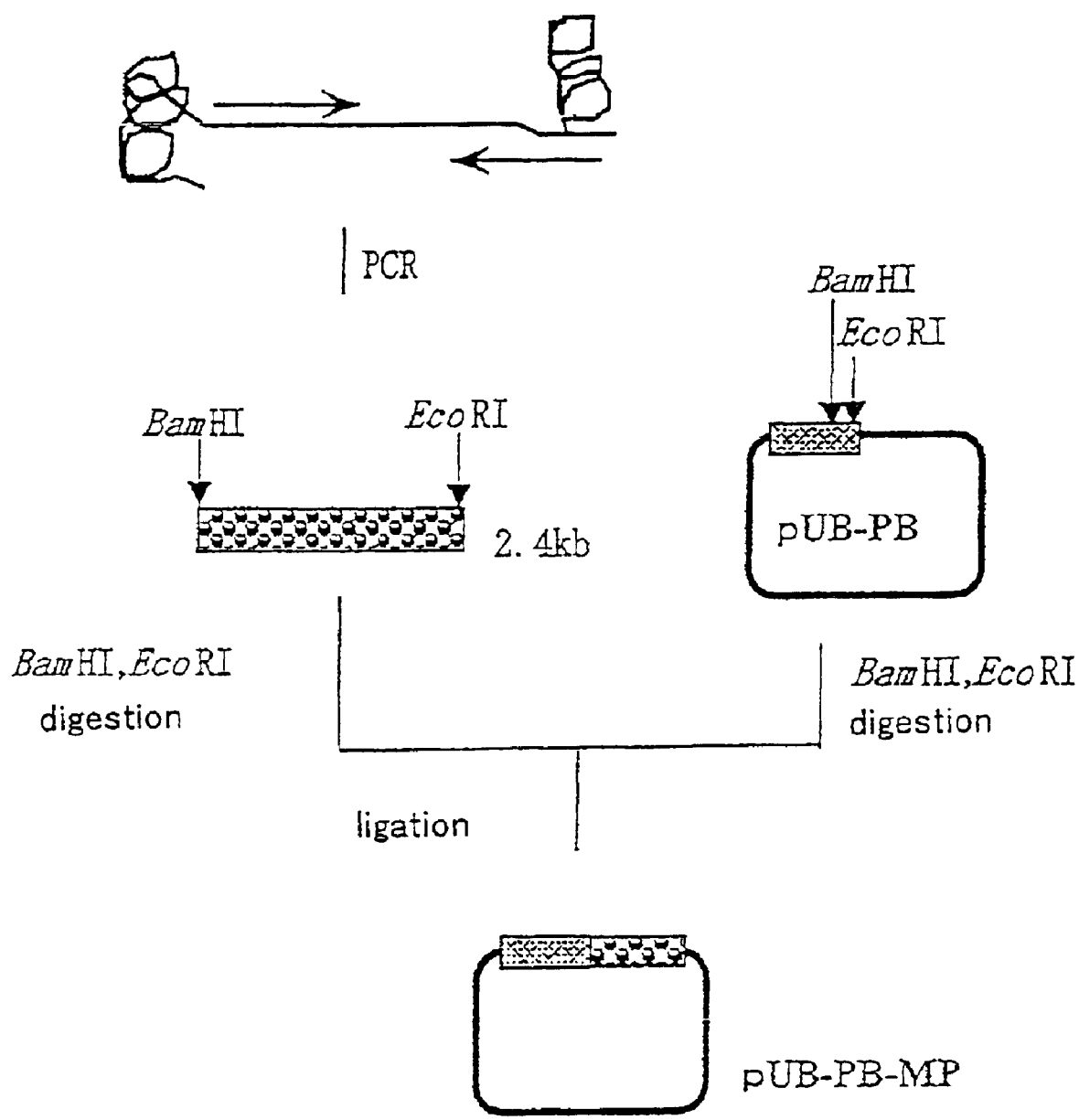
FIG. 3 is a schematic view of construction of an expression vector pUB-PB-MP of the present invention.

Separately, a plasmid pUB-PB was digested with BamHI and EcoRI, and then the 2.4 kbp fragment including the MPase structural gene was ligated thereto with T4DNA ligase, so that a plasmid pUB-PB-MP was obtained. FIG. 3 shows the construction of the MPase expression vector.

Figure 4:
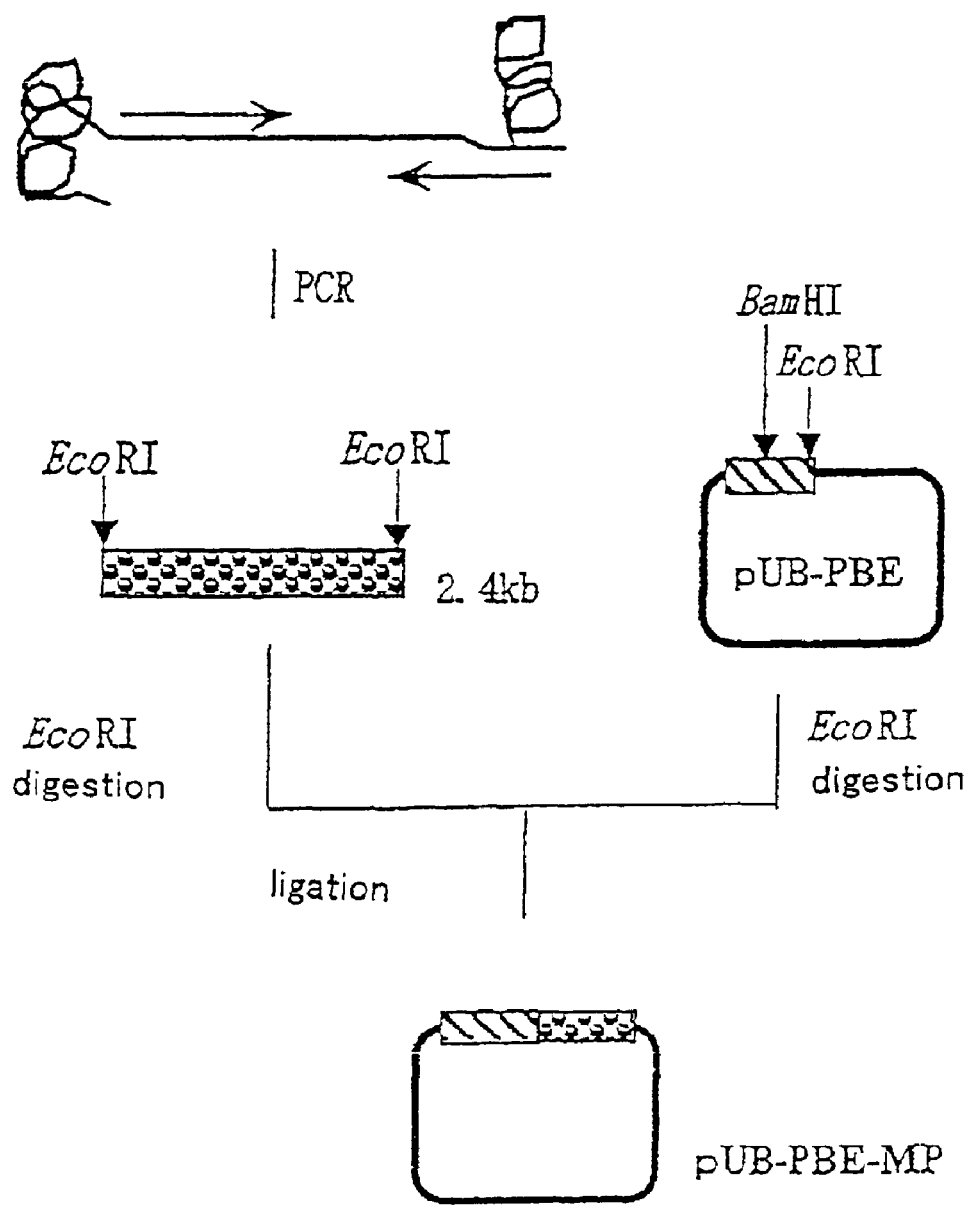
FIG. 4 is a schematic view of construction of an expression vector pUB-PBE-MP of the present invention.

Furthermore, PCR was performed in the same manner as above, using primers having the sequences indicated by Sequence ID Nos. 13 and 7 in the sequence listing. An amplified DNA fragment was cleaved with EcoRI, and a 2.4 kbp EcoRI-EcoRI fragment including an MPase structural gene was obtained. The obtained 2.4 kbp EcoRI fragment and a plasmid pUB-PBE digested by EcoRI were ligated to each other with T4DNA ligase, so that a plasmid pUB-PBE-MP was obtained. FIG. 4 shows the construction of the MPase expression vector.

Example 4

Construction of TPase Expression Vector

A TPase gene was obtained from chromosomal DNA of Bacillus stearothermophilus SK-1 strain (FERM P-14567), based on the description of Japanese Laid-Open Patent Publication (Tokkai) No. 10-327887. More specifically, a gene was amplified by PCR, using two kinds of primers having sequences of Sequence ID Nos. 8 and 9 in the sequence listing, cleaved with restriction enzymes BamHI and EcoRI, and then subjected to 0.8% agarose gel electrophoresis. Thus, a 2.4 kbp BamHI-EcoRI fragment was recovered. This fragment contained the structural gene of TPase.

Figure 5:
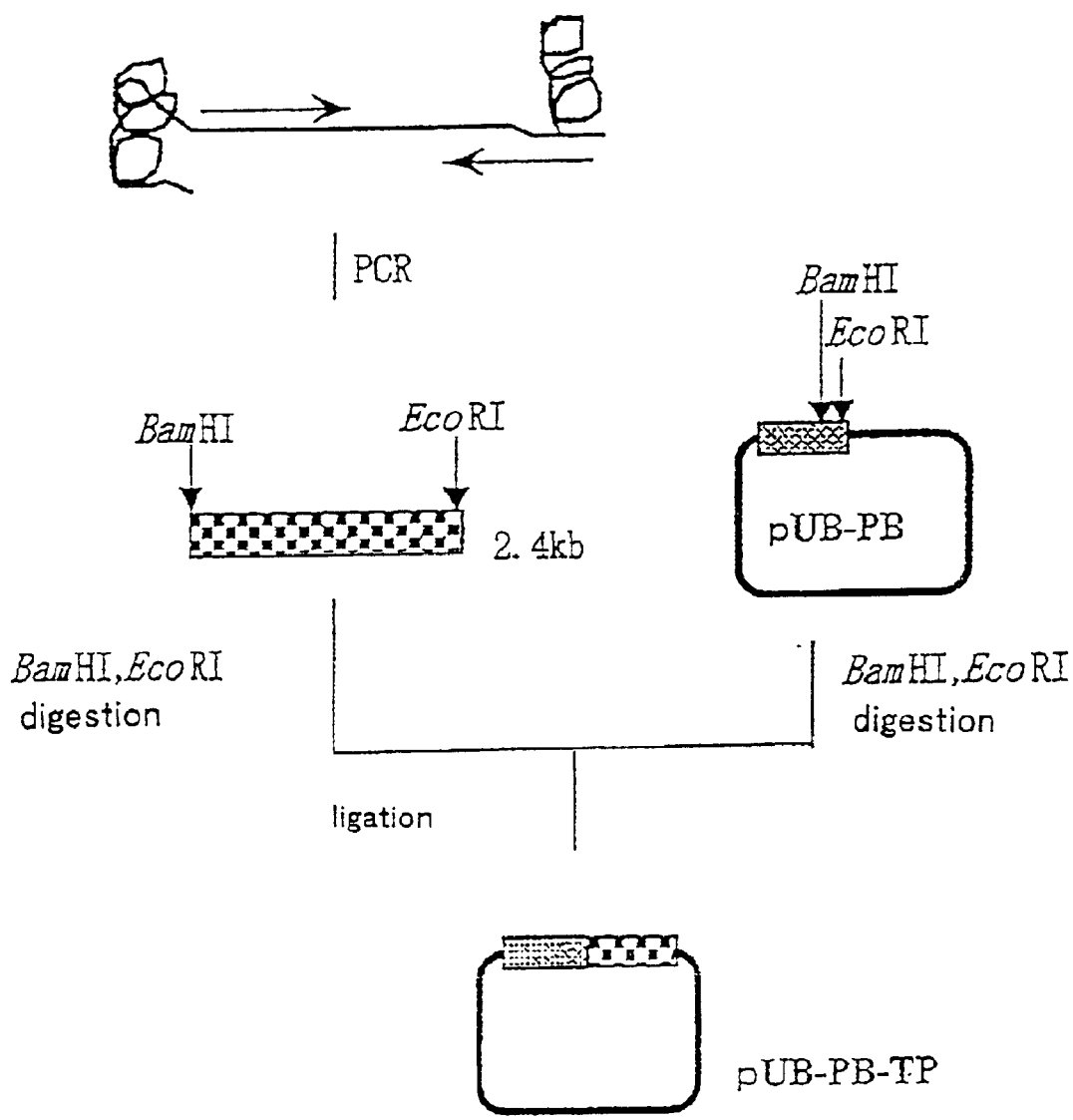
FIG. 5 is a schematic view of construction of an expression vector pUB-PB-TP of the present invention.

Separately, a plasmid pUB-PB was digested with BamHI and EcoRI, and then the 2.4 kbp fragment including the TPase structural gene was ligated thereto with T4DNA ligase, so that a plasmid pUB-PB-TP was obtained. FIG. 5 shows the construction of the TPase expression vector.

Figure 6:
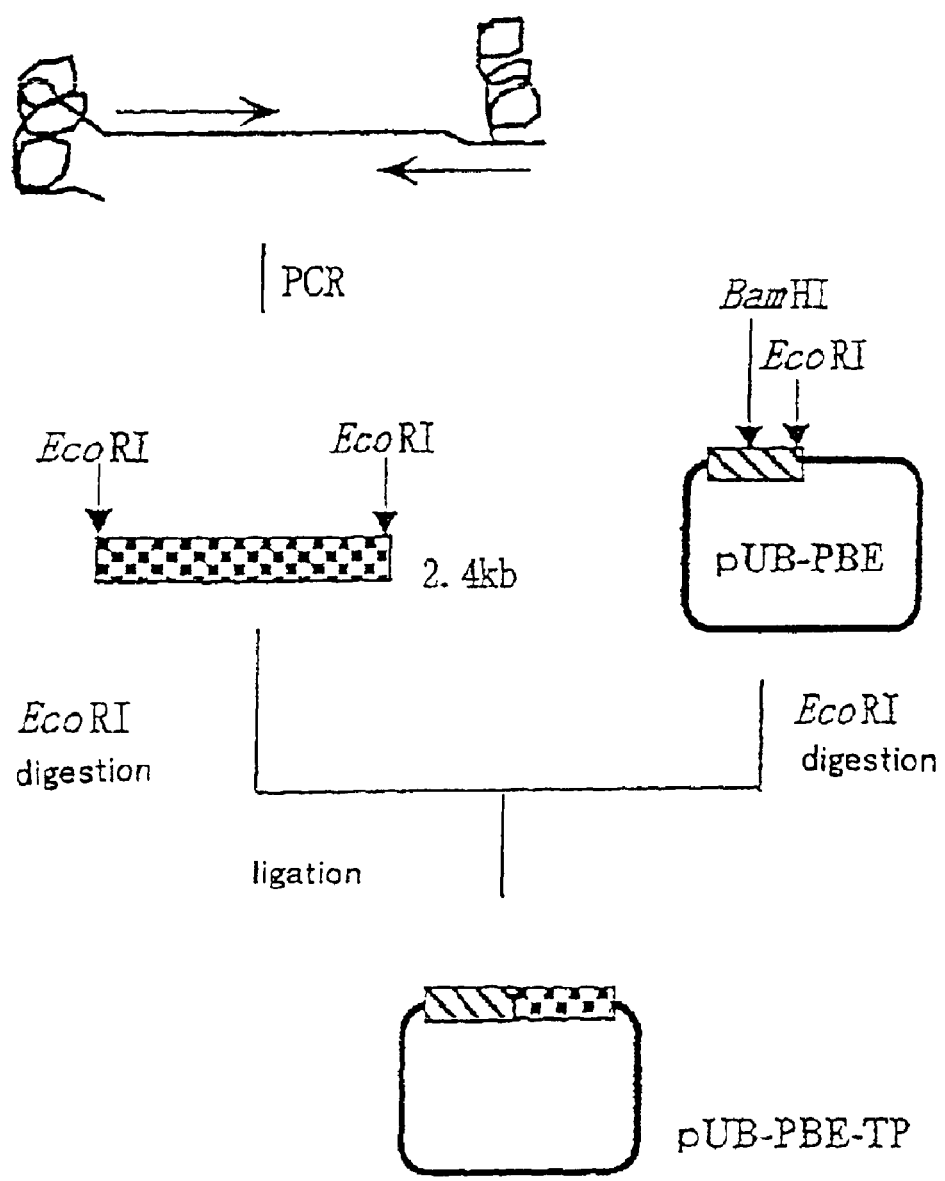
FIG. 6 is a schematic view of construction of an expression vector pUB-PBE-TP of the present invention.

Furthermore, PCR was performed in the same manner as above, using primers having the sequences indicated by Sequence ID Nos. 14 and 9 in the sequence listing. An amplified DNA fragment was cleaved with EcoRI, and a 2.4 kbp EcoRI-EcoRI fragment including a TPase structural gene was obtained. The obtained 2.4 kbp EcoRI fragment and a plasmid pUB-PBE digested with EcoRI were ligated to each other with T4DNA ligase, so that a plasmid pUB-PBE-TP was obtained. FIG. 6 shows the construction of the TPase expression vector.

Comparative Example 1

Construction of an MPase Expression Vector Having a Wild Type α-amylase Promoter The chromosomal DNA of Bacillus amyloliquefaciens IFO 15535 obtained in Example 1 was used to PCR amplification, using two types of primers having sequences of Sequence ID Nos. 3 and 10. The obtained fragment was phosphorylated with T4 polynucleotide kinase and blunt-ended by S1 nuclease. Thereafter, the fragment was digested with XbaI, subjected to 3.0% agarose gel electrophoresis, and then the DNA fragment was recovered. With these operations, a 0.25 kbp wild type α-amylase promoter fragment with an XbaI cleavage site at its 5' end and blunt-ended 3' terminal was obtained.

A gene was amplified by PCR from the template of chromosomal DNA of Bacillus species RK-1 strain (FERM P-15044) using two types of primers having sequences of Sequence ID Nos. 11 and 7. The obtained fragment was phosphorylated with T4 polynucleotide kinase and blunt-ended by S1 nuclease. Thereafter, the fragment was digested with EcoRI, subjected to 0.8% agarose gel electrophoresis, and then the DNA fragment was recovered. With these operations, a 2.4 kbp MPase gene that was blunt ended at its 5' terminal and had an EcoRI cleavage site in its 3'terminal was obtained.

Figure 7:
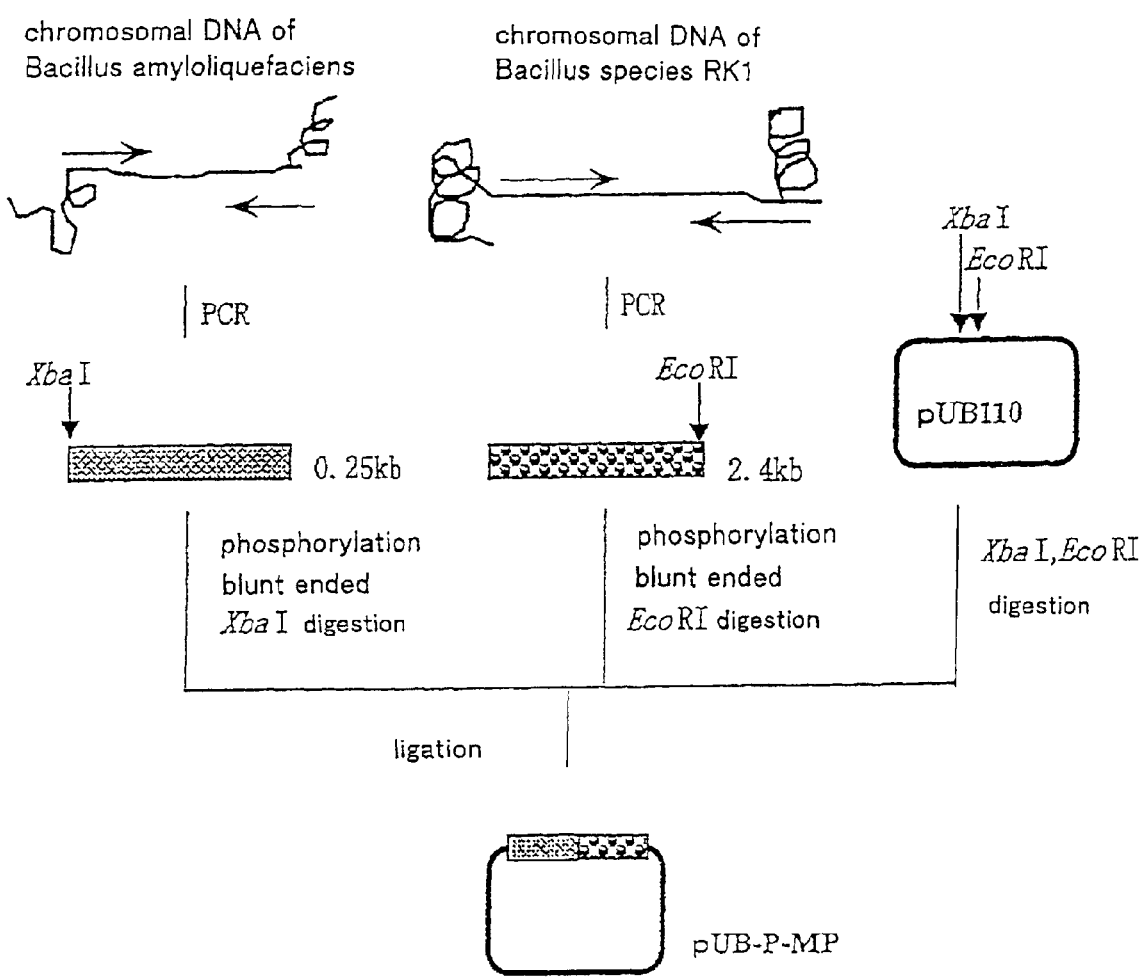
FIG. 7 is a schematic view of construction of an expression vector pUB-P-MP of Comparative Example 1.

Separately, a plasmid pUB110 was digested with restriction enzymes XbaI and EcoRI, and then the previously obtained promoter, 0.25 kbp DNA fragment and the 2.4 kbp fragment of MPase were ligated thereto. As a result, an expression vector pUB-P-MP was obtained. FIG. 7 shows the construction of the expression vector pUB-P-MP.

Comparative Example 2

Construction of a TPase Expression Vector Having a Wild Type α-Amylase Promoter

A gene was amplified by PCR from the chromosomal DNA of Bacillus stearothermophilus SK-1 strain (FERM P-14567) of in Example 4 using two kinds of primers having sequences of Sequence ID Nos. 12 and 9. The obtained fragment was phosphorylated with T4 polynucleotide kinase, and blunt ended by S1 nuclease. Thereafter, the fragment was cleaved with EcoRI, subjected to 0.8% agarose gel electrophoresis, and then a 2.4 kbp fragment including a TPase structural gene region was recovered. With these operations, a TPase gene that was blunt ended in its 5' terminal and had an EcoRI cleavage site in its 3' terminal was obtained.

Figure 8:
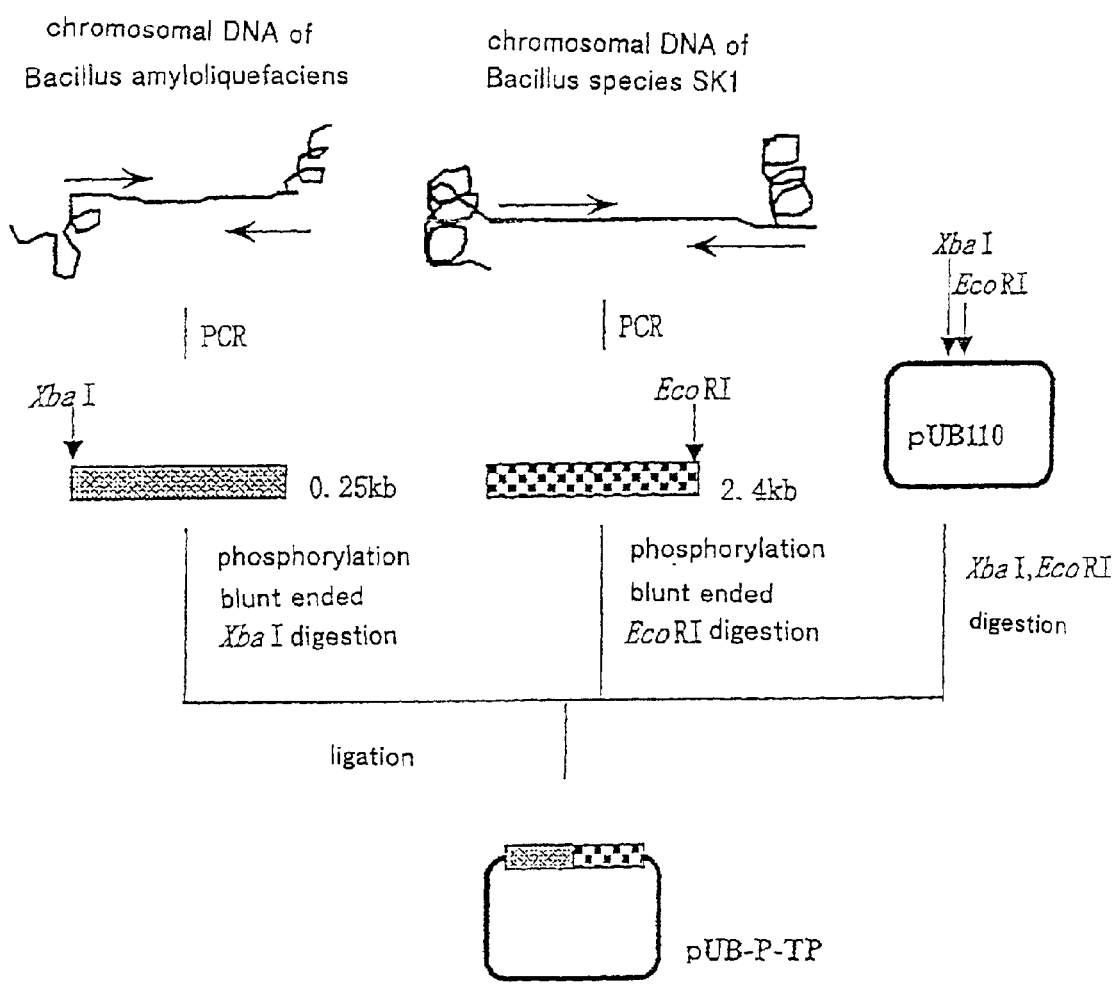
FIG. 8 is a schematic view of construction of an expression vector pUB-P-TP of Comparative Example 2.

Separately, a plasmid pUB110 was digested with restriction enzymes XbaI and EcoRI, and then a TPase expression vector PUB-P-TP was obtained in the same manner as in Comparative Example 1. FIG. 8 shows the construction of the expression vector pUB-P-TP.

Example 5

**Comparison in Activity Between MPase and TPase (Transformation and Expression of *Bacillus subtilis*)**

The expression vectors obtained in Examples 3 and 4 and Comparative Examples 1 and 2 were used to transform the strain of *Bacillus subtilis* 168 by a conventional method so that recombinant *Bacillus subtilis* strains, that is, *B.subtilis*/pUB-PB-MP, *B.subtilis*/pUB-PBE-MP, *B.subtilis*/pUB-PB-TP, *B.subtilis*/pUB-PBE-TP, *B.subtilis*/pUB-P-MP, and *B.subtilis*/pUB-P-TP were obtained. The first four recombinant *Bacillus subtilis* strains have an expression vector in which a restriction site is introduced into the promoter, and the last two have an expression vector having the natural promoter.

The obtained recombinant *Bacillus subtilis* strains were inoculated in a 100ml L medium (1% tryptone, 0.5% yeast extract, 0.5% NaCl, pH7.2, 10 μg kanamycin) and cultured at 37° C. over night. Then, 1 ml of the culture broth was taken, collected by centrifugation and suspended in a 0.85% NaCl aqueous solution. This collection and suspension was repeated to wash the bacteria. Then, the bacteria suspended in the 0.86% NaCl aqueous solution were inoculated in a 500 ml conical flask with baffles containing 100 ml 2×YT medium (1.6% tryptone, 1.0% yeast extract, 0.5% NaCl, pH7.2, 100 μM kanamycin) and cultured for 20 hours with a rotary shaker. After culturing, the cultured solution was subjected to a supersonic treatment to destroy the bacteria and the bacterial residue was removed by centrifugation to prepare a crude enzyme preparation. Then, the activity of MPase or TPase was measured. Table 1 shows the results.

TABLE 1

|  | recombinant microorganism having MPase gene | Restriction enzyme site in promoter | MPase activity Units/l | Increase rate (factor) |
|---|---|---|---|---|
| Example | *B. subtilis*/pUB-PB-MP | BamHI | 240,000 | 4.8 |
| Example | *B. subtilis*/pUB-PBE-MP | B,Sm,K,Sa,E(*1) | 240,000 | 4.8 |
| Com. Ex. | *B. subtilis*/pUB-P-MP | — | 50,000 | 1 |

|  | recombinant microorganism having TPase gene | Restriction enzyme site in promoter | TPase activity Units/l | Increase rate (factor) |
|---|---|---|---|---|
| Example | *B. subtilis*/pUB-PB-TP | BamHI | 300,000 | 4.3 |
| Example | *B. subtilis*/pUB-PBE-TP | B,Sm,K,Sa,E(*1) | 300,000 | 4.3 |
| Com. Ex. | *B. subtilis*/pUB-P-TP | — | 70,000 | 1 |

(*1) B:BamHI, Sm:SmaI, K:KpnI, Sa:SacI, E:EcoRI

For MPase and TPase, the productivity was improved by using α-amylase promoter having at least one restriction site in the 3' end. The activity of MPase and TPase was measured by the following method.

Measurement of MPase Activity

First, 0.4 ml of the crude enzyme preparation, 0.06 ml of 0.5M phosphate-citrate buffer (pH 6.0), 0.6 ml of 2 W/V % maltose and 0.14 ml of distilled water were mixed for maltose degradation reaction at 60° C. for 15 minutes. After the 15 minutes reaction, the reaction was stopped by 10 minutes boiling. An aliquot (0.02 ml) of the boiled reaction solution was added to 3 ml of a glucose test reagent Glucose CII-Test Wako (Wako Pure Chemical Industries, Ltd). The reaction mixture was incubated at room temperature for 20 minutes, followed by measurement of the absorbance at 505 nm with a spectrophotometer to determine the amount of the glucose in the reaction mixture. The amount of the enzymes that participate in phosphorolysis of 1 μmol of maltose for 1 minute based on the amount of the produced glucose was defined as one unit.

Measurement of Tpase Activity

In the same manner as in the case of MPase except that 2 W/V % trehalose was used as the substrate, the amount of glucose in a reaction solution was determined and the amount of the enzymes that participate in phosphorolysis of 1 μmol of trehalose for 1 minute was defined as one unit.

Example 6

Obtaining Mannose Isomerase (MIase) Gene and Construction of an Expression Cassette

An MIase used in the present invention is an enzyme produced from the strain that was isolated from soil in Hiroshima, Japan, and identified as Agrobacterium radiobactor M36 (FERM P-17377). This MIase gene was isolated and identified by shotgun cloning of the chromosomal DNA and detecting the MIase producing strain.

Preparation of Chromosomal DNA

An Agrobacterium radiobactor M36 strain (FERM P-17377) was inoculated in 5 ml of an LB liquid medium (1% polypeptone, 0.5% yeast extract, 0.5% NaCl, (pH7.0)) and cultured at 30° C. for 16 hours with shaking. This culture broth was transferred to a 500 ml flask with baffles containing 100 ml of an LB medium and cultured at 30° C. for 24 hours, and bacteria were collected by centrifugation.

The collected bacteria were suspended in a 0.1M tris-hydrochloric acid buffer (pH8.0) containing 0.1M EDTA. Then, lysozyme (Wako Pure Chemical Industries Ltd.) was added to this suspension in an amount of 4 mg/ml, and the suspension was shaken mildly at 37° C. for 30 minutes, followed by lyophilization at −80° C. for 30 minutes. After thawing, 0.1M tris-hydrochloric acid buffer (pH9.0) containing 1% SDS and 10 mM EDTA was added, and Protease K (Takara Shuzo Co. Ltd.) was further in added in an amount of 0.5 mg/ml, followed by incubation at 37° C. for 6 hours. A phenol solution saturated with 10 mM tris-hydrochloric acid buffer (pH8.0) containing 1 mM EDTA (hereinafter, referred to as TE buffer) was added to this treatment solution to remove protein and a supernatant was obtained. Then, chilled ethanol was added to the supernatant, and a produced precipitation of chromosomal DNA was recovered, immersed in 70% ethanol for 5 minutes and dissolved in a TE buffer. RNaseA (SIGMA Co.) was added to this dissolved solution in an amount of 10 μg/ml followed by reaction at 37° C. for 2 hours. Phenol was added to the reaction solution again to remove protein, and chilled ethanol was added. Then, a precipitated of chromosomal DNA was recovered. The obtained purified chromosomal DNA was immersed in 70% ethanol for 5 minutes, and dissolved in a TE buffer in an amount of 2 mg/ml to produce a chromosomal DNA solution.

Shotgun Screening: Selection of Transformant that Expresses MIase

About 40 units of restriction enzyme Sau3AI were added to 1 ml of the chromosomal DNA solution and incubated at 37° C. for one hour to produce partially hydrolyzed chromosomal DNA, followed by recovery of about 5 to 10 kbp DNA fragments using agarose gel electrophoresis.

Separately, a plasmid vector pBluescriptII SK (+) was cleaved with a restriction enzyme BamHI, and 0.1 μg of the plasmid vector and 1 μg of the recovered DNA fragments were ligated with DNA Ligation Kit (Takara Shuzo Co. Ltd.) and thus a recombinant plasmid was obtained. This plasmid was added to 100 μl of competent cell (Competent high *E. coli* JM109 (Toyo Boseki Co., Ltd.)) and was left standing under ice-cooling for 30 minutes, and then heated to 42° C. Then, an SOC medium (2% bacto tryptone, 0.5% bacto yeast extract, 10 mM NaCl, 2.5 mM KCl, 10 mM $MgCl_2$, 20 mM glucose, pH7.5) was added thereto, followed by incubation at 37° C. for one hour, and then the recombinant plasmid was introduced into *E. coli*.

A transformant was selected with an LB medium containing 100 μg/ml of ampicillin. The transformant was cultured on an LB agar medium (pH7.0) containing 50 μg/ml of 5-bromo-4-chloro-3-indolyl- β-D-galactoside and 250 μg/ml of isopropyl 1-thio-β-D-galactoside at 37° C. for 18 hours and a white colony was selected. The obtained white colony was suspended in Glucose CII-Test Wako (Wako Pure Chemical Industries Ltd.) containing 0.3% fructose and 2.5 mg/ml lysozyme and was left standing at 37° C. over night, and a colony that develops significant red according to visual observation was selected.

Whether or not the obtained transformant had expressed MIase was confirmed in the following manner. The transformant was inoculated in an LB medium containing 250 μg/ml of isopropyl 1-thio-β-D-galactoside and 100 μg/ml of ampicillin and cultured at 37° C. for 24 hours. After culturing, bacteria were collected by centrifugation, and washed twice with 25 ml of 100 mM phosphate buffer (pH7.0). The bacteria were suspended in 10 ml of phosphate buffer as above and subjected to ultrasonic treatment, followed by centrifugation so that a supernatant was obtained as a crude enzyme preparation. This crude enzyme preparation and 20% fructose solution were reacted at 50° C. for 24 hours and then production of mannose was confirmed by HPLC. The HPLC was performed under the following conditions.

Pump model: PU-1580 manufactured by Nihon Bunko Co. Ltd.

Column: CAPCELL PAK NH2 UG80 manufactured by Shiseido Co. Ltd.

Detector: RI-71 model Refraction Index Detector manufactured by Showa Denko K.K.

Eluent: acetonitrile: water=80:20

Flow rate: 1.0 ml/min

Under the above-described conditions, the retention time of mannose was 7.6 minutes, and the retention time of fructose was 6.7 minutes. In the reaction solution, a peak was observed at the retention time of 7.6 minutes, which confirmed that mannose was produced from fructose, that is, that the transformant has MIase activity.

Obtaining Deduced MIase Gene and Sequencing

Recombinant plasmid DNA was extracted from the obtained transformant and the nucleotide sequence was determined by a conventional method. About 7.0 kbp of the obtained sequence data was analyzed, and a fragment with about 1.5 kbp containing a sequence encoding protein was obtained. The DNA sequence of this fragment with about 1.5 kbp was shown in Sequence ID No. 15. It seems that atg from the $314^{th}$ to $316^{th}$ positions of Sequence ID No. 15 is an initiation codon, and taa from the $1559^{th}$ to $1561^{st}$ positions is the termination codon.

(Obtaining the Promoter of the Present Invention and Construction of an Expression Cassette)

An expression cassette having a promoter sequence having NdeI and XhoI restriction sites in the 3' end and the terminator sequence of α-amylase was prepared.

A DNA fragment (0.25 kbp XbaI-XhoI DNA fragment) to which NdeI and XhoI restriction sites were introduced downstream of Sequence ID No. 1 (promoter sequence) was obtained in the same manner as in Example 1, except that a primer having the sequence shown in Sequence ID No. 16 was used instead of Sequence ID No. 4.

Separately, two kinds of primers having sequences of Sequence ID Nos. 17 and 18 in the sequence listing were synthesized based on the sequence of the α-amylase terminator sequence described in Gene, 15, 43-(1981) for amplification by PCR. The gene fragment amplified by PCR was cleaved with restriction enzymes XhoI and EcoRI, and then subjected to 3.0% agarose gel electrophoresis. Thus, a 0.28 kbp XhoI-EcoRI fragment including the terminator region of α-amylase was recovered from the agarose gel. The sequence of this fragment is shown Sequence ID No. 19.

Figure 9:
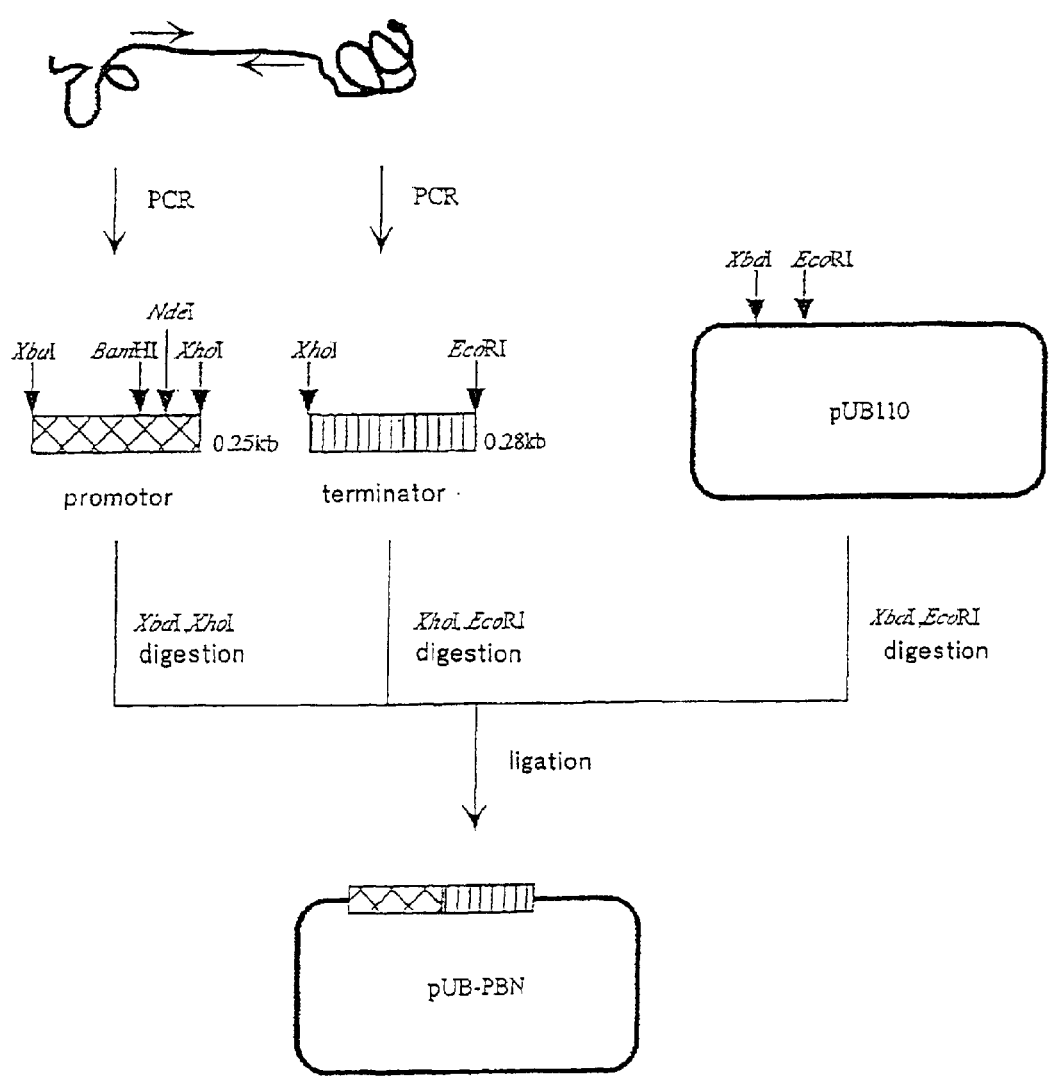
FIG. 9 is a schematic view of construction of an expression cassette pUB-PBN of the present invention.

A plasmid pUB110 (manufactured by SIGMA Co.) was digested by XbaI-EcoRI, and then the obtained promoter sequence (0.25 kbp XbaI-XhoI fragment) and the terminator sequence (0.28 kbp XhoI-EcoRI fragment) were ligated thereto with T4DNA ligase, so that an expression cassette pUB-PBN was obtained (FIG. 9).

Construction of MIase Expression Vector

An MIase gene was amplified by PCR with chromosomal DNA of Agrobacterium radiobacter M36 strain (FERM P-17377) using two types of primers having sequences of Sequence ID Nos. 20 and 21 in the sequence listing, and cleaved with restriction enzymes NdeI and XhoI, and then subjected to 0.8% agarose gel electrophoresis. Thus, a 1.2 kbp NdeI-XhoI fragment was recovered. This fragment included an MIase structural gene constituted by the $341^{th}$ to $1558^{th}$ positions of Sequence ID No. 15.

Figure 10:
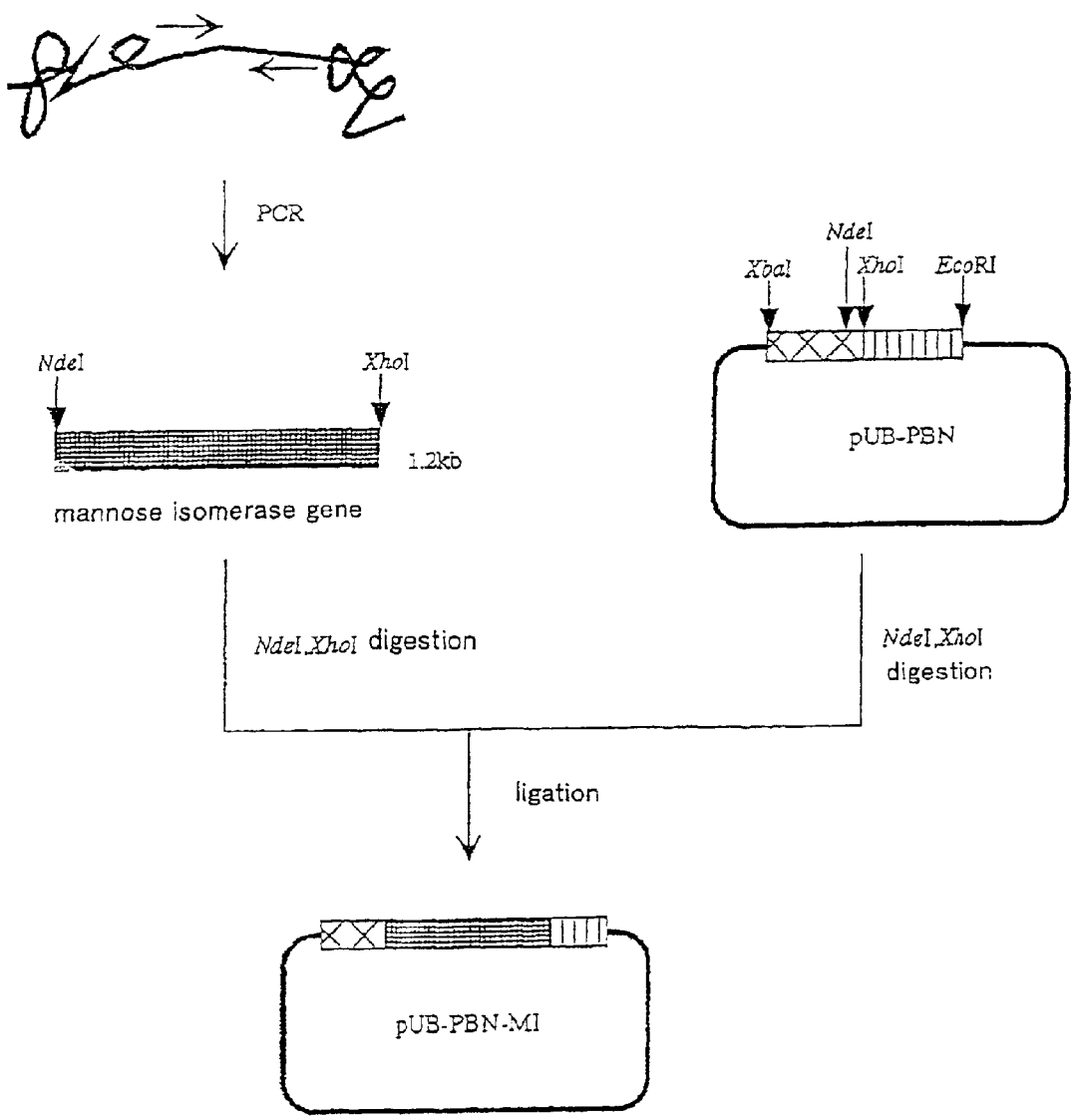
FIG. 10 is a schematic view of construction of an expression vector pUB-PBN-MI of the present invention.

The obtained plasmid pUB-PBN was digested with NdeI and XhoI, and then the 1.2 kbp fragment including the MIase structural gene was ligated thereto with T4DNA ligase, so that a plasmid pUB-PBN-MI was obtained. FIG. 10 shows the construction of the MIase expression vector.

Comparative Example 3

For comparison, an MIase expression vector having the α-amylase promoter of a wild type *Bacillus amyloliquefaciens* was prepared.

A gene was obtained from the chromosomal DNA of an Agrobacterium radiobacter M36 strain (FERM P-17377) and amplified by PCR, using two types of primers having sequences of Sequence ID Nos. 22 and 21. The obtained fragment was phosphorylated with T4 polynucleotide kinase, and blunt ended by S1 nuclease. Thereafter, the fragment was cleaved with XhoI, subjected to 0.8% agarose gel electrophoresis, and the DNA fragment was recovered. With these operations, a 1.2 kbp MIase gene that was blunt ended at its 5' terminal and had an XhoI cleavage site in its 3' terminal was obtained.

Figure 11:
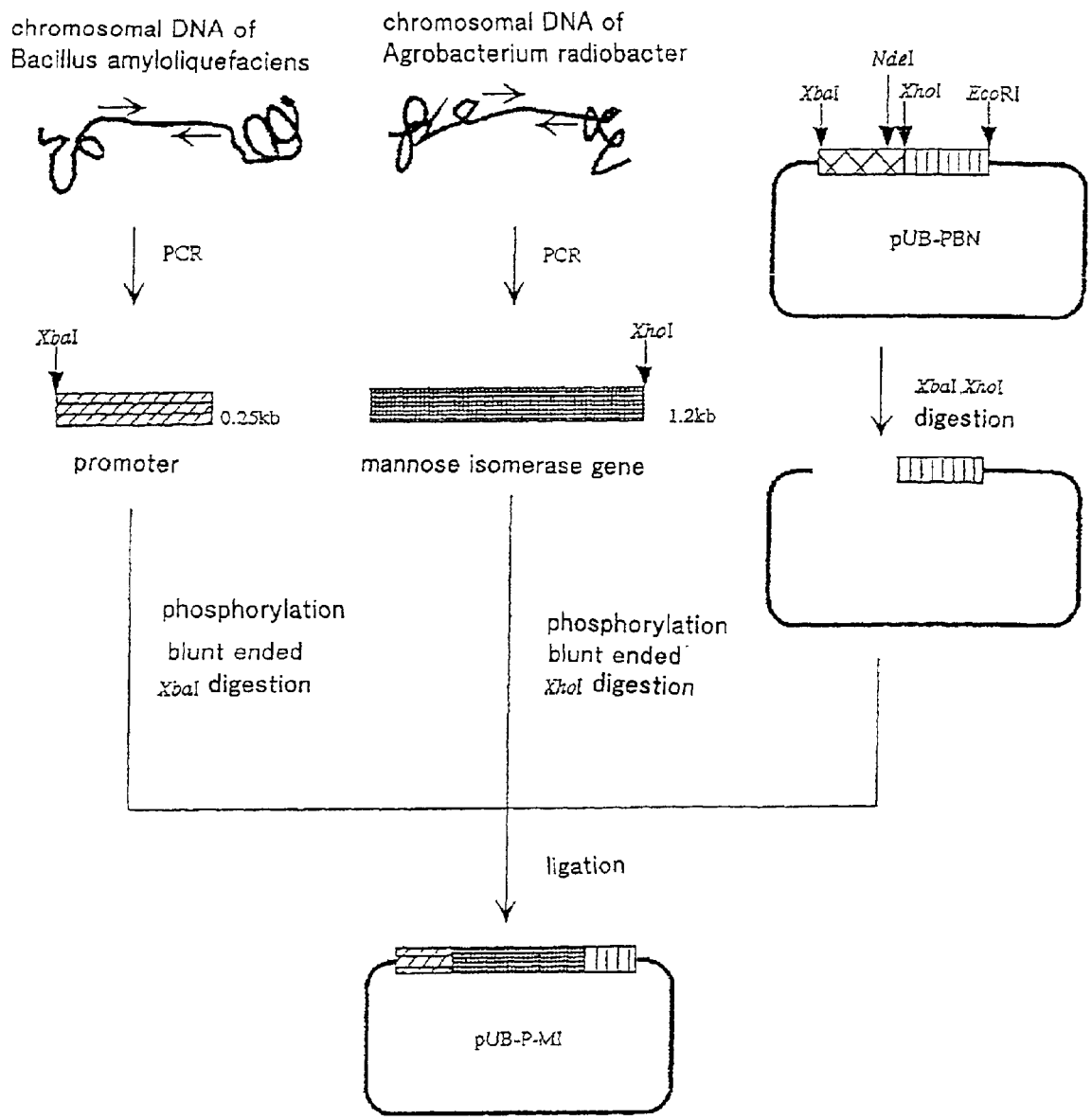
FIG. 11 is a schematic view of construction of an expression vector pUB-P-MI of the present invention.

Separately, the above-obtained plasmid pUB-PBN was digested with XbaI and XhoI, subjected to 0.8% agarose gel electrophoresis, and thus a DNA fragment free from the α-amylase promoter was recovered. The 0.25 kbp DNA fragment of the wild type α-amylase promoter obtained in Comparative Example 1 and the 1.2 kbp fragment of the MIase gene were ligated to the DNA fragment of the pUB-PT. As a result, an expression vector pUB-P-MI was obtained. FIG. 11 shows the construction of the expression vector pUB-P-MI.

Example 7

Comparison of MIase Activity

Transformation into *Bacillus subtilis* and expression

Using the expression vector obtained in Example 6 and Comparative Example 3, *Bacillus subtilis* 168 was transformed by a conventional method, and thus recombinant *Bacillus subtilis* strains, *B.subtilis*/pUB-PBN-MI and *B.subtilis*/pUB-P-MI were obtained. The former has an expression vector in which a restriction enzyme site is introduced into the promoter, and the latter has an expression vector having the natural promoter.

The obtained recombinant *Bacillus subtilis* strains were used to prepare a crude enzyme preparation in the same manner as in Example 5, and the activity of the MIase was measured. Table 2 shows the results.

TABLE 2

| | MIase gene recombinant microorganism | Restriction enzyme sites in promoter | MIase activity Units/l | Increase rate (factor) |
|---|---|---|---|---|
| Example | *B. subtilis*/pUB-PBN-MI | BamHI,NdeI | 730,000 | 6.9 |
| Com. Ex. | *B. subtilis*/pUB-P-MI | — | 106,000 | 1 |

As seen from the results, the MIase had activity 7 times higher than that of the natural type, and the productivity was improved by using the α-amylase promoter having a restriction enzyme cleavage site in the 3' end as in the cases of MPase and TPase.

The activity of the MIase was measured by the following method. First, 200 μl of an enzyme solution that had been diluted as appropriate was added to 200 μl of 200 mM mannose solution dissolved in a 100 mM phosphate buffer (pH7.0), and an enzyme reaction was performed at 50° C. Then, the enzyme reaction was stopped by boiling for 10 minutes, and the composition of the saccharide was analyzed by HPLC. The amount of the enzymes that produce 1 μmol of fructose for 1 minute under these conditions was defined as one unit.

Industrial Applicability

It was found that introducing a restriction site into the 3' end of α-amylase promoter improves the activity of the promoter. This promoter has a high activity and since it has a restriction site, a foreign gene easily can be inserted therein, so that this promoter is useful for substance production.

---

What is claimed is:

1. A promoter of α-amylase derived from *Bacillus amyloliquefaciens*, wherein the promoter has a sequence of Sequence ID No. 1 that has a restriction site for BamHI in the 3' terminus.

2. An expression cassette comprising the promoter sequence according to claim 1.

3. An expression vector, wherein a polynucleotide encoding a protein is inserted into the BamHI restriction site of the expression cassette of claim 2.

4. A recombinant microorganism transformed with the expression vector according to claim 3.

5. A method for producing a protein comprising the step of culturing the recombinant microorganism according to claim 4.

6. A promoter of α-amylase derived from *Bacillus amyloliquefaciens*, wherein the promoter has a sequence of ID No. 2 that has restriction sites for BamHI, SmaI, KpnI SacI and EcoRI in this order from 5' end in the 3' terminus.

7. An expression cassette comprising the promoter sequence according to claim 6.

8. An expression vector, wherein a polynucleotide encoding a protein is inserted into one of the restriction sites of the expression cassette of claim 7.

9. A recombinant microorganism a transformed with the expression vector according to claim 8.

10. A method for producing a protein comprising the step of culturing the recombinant microorganism according to claim 9.

* * * * *

UNITED STATES PATENT AND TRADEMARK OFFICE
CERTIFICATE OF CORRECTION

PATENT NO. : 6,770,475 B1
DATED : August 3, 2004
INVENTOR(S) : Inoue et al.

It is certified that error appears in the above-identified patent and that said Letters Patent is hereby corrected as shown below:

Title page,
Item [56], References Cited, add:
-- U.S. PATENT DOCUMENTS
5,721,137   B1   Frascotti et al.   02/1998 --
FOREIGN PATENT DOCUMENTS, add:

| | | | |
|---|---|---|---|
| -- | EP | A2 | 681027 | 11/1995 |
| | JP | A | 4-278091 | 10/1992 |
| | JP | A | 59-205996 | 11/1984 |
| | JP | A | 62-215393 | 09/1987 |
| | JP | A | 3-206889 | 09/1991 |
| | JP | B2 | 60-262663 | 09/1994 |
| | JP | A | 7-155183 | 06/1995 |
| | JP | A | 10-262683 | 10/1998 |
| | WO | A1 | 92/03561 | 03/1992 |
| | WO | A1 | 93/10249 | 05/1993 -- |

OTHER PUBLICATIONS, add:
-- Lehtovaara, Päivi et al., "In vivo transcription initiation and termination sites of an α-amylase gene from *Bacillus amyloliquefaciens* cloned in *Bacillus subtilis*", GENE, Oct. 1984, pp. 11-16, Vol. 30 nos. 1, 2, 3, Elsevier Science Publishers.

Horinouchi, Sueharu et al., "Construction and characterization of multicopy expression-vectors in *Streptomyces* spp", MGG Molecular & General Genetics, Dec. 11, 1987, pp. 468-475, Vol. 210, No. 3.

Palva, Ilkka et al., "Nucleotide sequence of the promotor and $NH_2$-terminal signal peptide region of the α-amylase gene from *Bacillus amyloliquefaciens*", GENE, 1981, Vol. 15, pp. 43-51, Elsevier/North-Holland Biomedical Press.

Keggins, Kathleen M. et al., "Molecular cloning of genetically active fragments of *Bacillus* DNA in *Bacillus subtilis* and properties of the vector plasmid pUB110", Proc. Nat. Acad. Sci. USA, March 1978, Vol .75, No. 3, pp. 1423-1427, Genetics.

Ehrlich, S. D., "Replication and expression of plasmids from *Staphylococcus aureau* in *Bacillus substilis*", Proc. Natl. Acad. Sci. USA, April 1977, Vol. 74, No. 4, pp. 1680-1682, Genetics.

Ishiwa, Hiromi et al., "New shuttle vectors for *Escherichia coli and Bacillus subtilis*. II. Plasmid pHY300PLK, a mulipurpose cloning vector with a polylinker, derived from pHY460", Jpn. J. Genet, 1985, Vol. 60, pp. 235-243.

UNITED STATES PATENT AND TRADEMARK OFFICE
CERTIFICATE OF CORRECTION

PATENT NO. : 6,770,475 B1
DATED : August 3, 2004
INVENTOR(S) : Inoue et al.

It is certified that error appears in the above-identified patent and that said Letters Patent is hereby corrected as shown below:

Title page, (cont'd)
Bolivar, Francisco et al., "Construction and Charactization of New Cloning Vehicles. II. A Multipurpose Cloning System", GENE, 1977, Vol. 2, pp. 95-113, Elsevier/North Holland Biomedical Press, Amsterdam. --

Column 24,
Line 4, "microorganism a transformed" should read -- microorganism transformed --.

Signed and Sealed this

Fifteenth Day of March, 2005

JON W. DUDAS
*Director of the United States Patent and Trademark Office*

SEQUENCE LISTING

<160> NUMBER OF SEQ ID NOS: 22

<210> SEQ ID NO 1
<211> LENGTH: 249
<212> TYPE: DNA
<213> ORGANISM: Bacillus amyloliquefaciens

<400> SEQUENCE: 1

```
gccccgcaca tacgaaaaga ctggctgaaa acattgagcc tttgatgact gatgatttgg      60
ctgaagaagt ggatcgattg tttgagaaaa gaagaagacc ataaaaatac cttgtctgtc     120
atcagacagg gtatttttta tgctgtccag actgtccgct gtgtaaaaaa taggaataaa     180 gggggttgt tattatttta ctgatatgta aaatataatt tgtataagaa aatgagaggg     240
agaggatcc                                                             249
```

<210> SEQ ID NO 2
<211> LENGTH: 270
<212> TYPE: DNA
<213> ORGANISM: Bacillus amyloliquefaciens

<400> SEQUENCE: 2

```
gccccgcaca tacgaaaaga ctggctgaaa acattgagcc tttgatgact gatgatttgg      60
ctgaagaagt ggatcgattg tttgagaaaa gaagaagacc ataaaaatac cttgtctgtc     120
atcagacagg gtatttttta tgctgtccag actgtccgct gtgtaaaaaa taggaataaa     180 gggggttgt tattatttta ctgatatgta aaatataatt tgtataagaa aatgagaggg     240 agaggatcc ccgggtaccga gctcgaattc                                     270
```

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 3
cgctctagag ccccgcacat acgaaaaga                                        29

<210> SEQ ID NO 4
<211> LENGTH: 35
<212> TYPE: DNA
<213> ORGANISM: Artificial Sequence
<220> FEATURE:
<223> OTHER INFORMATION: Description of Artificial Sequence: Example of
      a primer for introducing a restriction site

<400> SEQUENCE: 4
cgcgaattcg gatcctctcc ctctcatttt cttat                                 35

<210> SEQ ID NO 5
<211> LENGTH: 50
<212> TYPE: DNA
<213> ORGANISM: Artificial Sequence
<220> FEATURE:
<223> OTHER INFORMATION: Description of Artificial Sequence: Example of
      a primer for introducing a restriction site

<400> SEQUENCE: 5
cgcgaattcg agctcggtac ccggggatcc tctccctctc attttcttat                 50

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 6
cgcggatcca tgtattacaa caggttgtt                                        29

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 7
cgcgaattct cacacatact ccttcgtat                                        29

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 8
cgcggatcca tgtcttggtc aattagctc                                        29

<210> SEQ ID NO 9
<211> LENGTH: 29
<212> TYPE: DNA
<213> ORGANISM: Artificial Sequence

```
<220> FEATURE:
<223> OTHER INFORMATION: Description of Artificial Sequence: Primer

<400> SEQUENCE: 9
aaagaattct taatcaacac gcccgttat                              29

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 10
gtttcctctc cctctcattt tcttat                                 26

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 11
atgtattaca acaggttgtt                                        20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 12
atgtcttggt caattagctc                                        20

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 13
cgcgaattca tgtattacaa caggttgtt                              29

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 14
cgcgaattca tgtcttggtc aattagctc                              29

<210> SEQ ID NO 15
<211> LENGTH: 1581
<212> TYPE: DNA
<213> ORGANISM: Agrobacterium radiobacter M36
<220> FEATURE:
<221> NAME/KEY: Promoter
<222> LOCATION: 314..316
<221> NAME/KEY: Terminator
<222> LOCATION: 1559..1561
<221> NAME/KEY: Gene
<222> LOCATION: 341..1558
```

<223> OTHER INFORMATION: MIase structural gene

<400> SEQUENCE: 15

```
gatctgcgtg cccatggcac cgtcgagaat gaggatgcgt tcgctggcag cctcgcgcag      60
cgccttgaaa atttccgcgc cgtcgcgctt tgcccgttca gggccaaaca gatcgtcaaa     120
cacgggcaca ctcctcattt cgatttgcaa gatcgcaagt cgtcaagtca cataaagata    180
tgtttatgtc aatatatctt caagggacag gcatggcttt cgtcgttgc gtcacgttac      240
gaaatatcgc tgacagatga caggtttata cggcaaggat ataagccgaa gcagcaaacg    300
catggaggac gcaatgcccg aagacgatca acagccgc aactggaata ccctgccctg      360
gcaccgccag tggctggtga acaggccga gggacttttc gacttcttcc agtatcgcgc     420
cctcaatccc gccggcggtt tcttcgatcc cgacgccaag ggcgcgccgc tgcaggcaaa     480
cgatcccgtg cgcggcatcc atgcctctgc gcgcatggtg cattgcttct ccatcggcca    540
cctgctcggc cggccgggct gcggcgatat cgtcgaccac ggcatgacct atctctggaa    600
caaacaccgc gatggcgaac atggcggtta tttctggcag gtgaacgatg ccggcccagt    660
ggacgccacc aagcagggtt atggccacgc cttcgtgctt ctggccgcct cttccgccaa    720
gaccgtcggc caccgctgg ccgaccggat gctggctgat attaccgaag tgctggaaag     780
tcgtttctgg gaagaaaaac atggcgccat cgccgaggaa ttcaatcgcg actggtcgcc    840
catcgacaat tatcgcggcc agaactccaa tatgcacctc accgaagcgc tgatggccgc    900
ctatgaggtg accggcgaca ataactatct cagcaaggcc gaacgcatcg ccgatctcgt    960
catccgtcgc cgcgccggcg agctggattt ccgcgtgccc gagcatttcg acgacaactg   1020
gacgctggac aaggactatc gcggcaacga aatgttccgc ccctccggct ccaccccgg    1080
ccactggctg aatgggcgc gtctcatcct gcaattgtgg atactgggcg aacgccgcca    1140
cgactggatg ccggtcgcgg ccaaatccct cttcgtgcag tccatggcgc tgggctggga   1200
ccgggaaaag ggcggcttct tttatacgct ggactggaat gacaatcccg acaagcgggc   1260
aaagctctgg tggcccatgt ccgaggcgg gggtgcggcc catttcctca acgagaacct    1320
gccggcggat ggcttctacg aagacagcta tcgtcgcatc tggagcacca tcgccaacaa   1380
cttcatcgac catgccaatg gcggctggca tgaggaactg acggaagatc tggttcccgc   1440
ccacacgcta ttcccaggca aggcgatat ctaccatgcg ctccaggcct gcctcatccc    1500
gctttttccg gcgacgggca gcctgacgaa ggtgatcaag gaaagcggcg gggattatta   1560
aggcgctctg cggccaatag c                                             1581
```

<210> SEQ ID NO 16
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 16

```
gcatctcgag catatgcgga tcctctccct ctcattttc                             39
```

<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 17

```
gcatctcgag ggtaataaaa aaacacctcc a                                    31

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 18
gcatgaattc aaagcagcga tcccgatgaa                                      30

<210> SEQ ID NO 19
<211> LENGTH: 283
<212> TYPE: DNA
<213> ORGANISM: Bacillus amyloliquefaciens

<400> SEQUENCE: 19
ctcgagggta ataaaaaaac acctccaagc tgagtgcggg tatcagcttg gaggtgcgtt      60
tattttttca gccgtatgac aaggtcggca tcaggtgtga caaatacggt atgctggctg    120
tcataggtga caaatccggg ttttgcgccg tttggctttt tcacatgtct gattttgta    180 taatcaacag gcacggagcc ggaatctttc gccttggaaa ataagcggc gatcgtagct    240 gcttccaata tggattgttc atcgggatcg ctgctttgaa ttc                      283

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 20
gcatcatatg cccgaagacg atcacaac                                        28

<210> SEQ ID NO 21
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 21
gcatctcgag ttaataatcc ccgccgcttt c                                    31

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 22
atgcccgaag acgatcacaa c                                               21
```